(12) United States Patent
Jonckheere et al.

(10) Patent No.: US 8,200,310 B2
(45) Date of Patent: Jun. 12, 2012

(54) SPINAL INJURY IMAGING BY MAGNETICALLY LEVITATED SENSORS

(75) Inventors: Edmond Jonckheere, Rossmoor, CA (US); Mingji Lou, Lexington, KY (US)

(73) Assignee: University of Southern California, Los Angeles, CA (US)

( * ) Notice: Subject to any disclaimer, the term of this patent is extended or adjusted under 35 U.S.C. 154(b) by 426 days.

(21) Appl. No.: 12/273,354

(22) Filed: Nov. 18, 2008

(65) Prior Publication Data

US 2009/0131736 A1     May 21, 2009

Related U.S. Application Data

(60) Provisional application No. 60/989,051, filed on Nov. 19, 2007.

(51) Int. Cl.
*A61B 5/05* (2006.01)
(52) U.S. Cl. .......... 600/407; 600/409; 428/403
(58) Field of Classification Search ........ 600/9–11, 600/407, 409, 420, 424, 427, 431, 410; 977/810, 977/836, 838; 324/207.2, 246, 259; 428/384, 428/403; 427/217
See application file for complete search history.

(56) References Cited

U.S. PATENT DOCUMENTS

| | | | | |
|---|---|---|---|---|
| 5,434,901 A * | 7/1995 | Nagai et al. | | 378/43 |
| 6,132,360 A * | 10/2000 | Halpern | | 600/9 |
| 6,541,617 B1 * | 4/2003 | Bamdad | | 536/23.1 |
| 7,250,757 B1 * | 7/2007 | Tiernan | | 324/238 |
| 2003/0158474 A1* | 8/2003 | Scherer et al. | | 600/409 |
| 2004/0086550 A1* | 5/2004 | Roorda et al. | | 424/448 |
| 2004/0086572 A1* | 5/2004 | Dailey et al. | | 424/489 |
| 2006/0286379 A1* | 12/2006 | Gao | | 428/403 |
| 2008/0241264 A1* | 10/2008 | Solomon | | 424/490 |

OTHER PUBLICATIONS

Ankar et al. Magnetically controlled sensor swarms. Sensors and Actuators B:Chemical, 2007, vol. 121, Issue 1, pp. 83-92.
Freitas Jr. Progress in Nanomedicine and Medical Nanorobotics. Handbook of theoretical and Computational Nanotechnology. 2005. Chapter 32, pp. 619-672.
International Search Report for PCT Application Serial No. PCT/US08/083922, mailed on Jan. 15, 2009.
Jonckheere et. al. Spinal Injury Imaging by Magnetically Levitated Sensors (SPIMALS) & Automation Microscopy with the Magnetically Controlled Nano-manipulators (AMMCN) Progress Report (Jun. 21, 2008).

(Continued)

*Primary Examiner* — James Kish
*Assistant Examiner* — Michael N Fisher
(74) *Attorney, Agent, or Firm* — McDermott Will & Emery LLP

(57) ABSTRACT

A system for detecting a spinal injury region containing injured spinal nerve cells may include a swarm of nanosensors that are configured to detect chemical signals released by the injured spinal nerve cells, and are coated with a magnetic material. A magnetic field generator may controllably generate a magnetic field so as to magnetically levitate the magnetically coated nanosensors. An imaging subsystem may detect the positions of the nanosensors. A controller may control the intensity and direction of the magnetic field in a feedback loop, in response to the detected positions of the nanosensors, so that the attractive force that attracts each nanosensor toward the injured spinal cell as a result of the chemical affinity of the nanosensor is iteratively supplemented by the magnetic levitation force applied to that nanosensor, until substantially all of the nanosensors are agglutinated around the spinal injury region.

10 Claims, 5 Drawing Sheets

OTHER PUBLICATIONS

Jonckheere et. al. Spinal Injury Imaging by Magnetically Levitated Sensors (SPIMALS) & Automation Microscopy with the Magnetically Controlled Nano-manipulators (AMMCN) Progress Report (Aug. 8, 2008).

Pankhurst et al. Applications of magnetic nanoparticles in medicine. Journal of Physics D: Applied Physics, 2003, pp. R167-R181.

Royo et. al. Specific AAV Serotypes Stably Transduce Hippocampal and Cortical Cultures with High Efficiency and Low Toxicity. Neurologic: Applications to Brain and Eye; Vector Development; Immune Responses. Modecular Therapy vol. 13, Supplement May 1, 2006, p. S347.

Wang et al. Magnetic resonance tracking of nanoparticle labeled neural stem cells in a rat's spinal cord. Institute of Physics Publishing, Nanotechnology 17 (2006), pp. 1911-1915.

* cited by examiner

SPINAL INJURY IMAGING BY MAGNETICALLY LEVITATED SENSORS

CROSS REFERENCE TO RELATED APPLICATION

This application claims the benefit of priority under 35 U.S.C. §119(e) from co-pending, commonly owned U.S. provisional patent application Ser. No. 60/989,051 (the '051 provisional application"), entitled "Spinal Injury Imaging By Magnetically Levitated Sensors," filed Nov. 19, 2007. The content of the '051 provisional application is incorporated herein by reference in its entirety as though fully set forth.

BACKGROUND

Traditionally, clinicians and researchers have incorporated surface electromyography (sEMG) as a diagnostic tool for assessing muscle and even central nervous system (CNS) functions. Recently, a switching dynamic model was developed of the sEMG signals generated during a condition in which the mechanical attachment of the spinal dura to the cervical vertebra creates an unstable nonlinear feedback coupling between the biomechanics of the spine and the CNS. The external visual appearance of this instability may include an involuntarily controlled rocking motion of the spine that resembles butterfly swimming. This motion may produce an intensive stimulation of the nervous system. Moreover, an analysis of the sEMG signals generated by this repetitive motion on spinal cord injury patients may show that it produces some regeneration in the central nervous system.

One problem, however, is that the noninvasive sEMG electrodes collect the nervous signals only indirectly and corrupt them with noise. As such, the sEMG signals are sometimes very difficult to analyze.

SUMMARY

A system for detecting a spinal injury region containing injured spinal nerve cells may include a swarm of nanosensors that are configured to detect chemical signals released by the injured spinal nerve cells, and are coated with a magnetic material. A magnetic field generating subsystem, including without limitation a system of solenoids, may controllably generate a magnetic field so as to magnetically levitate the magnetically coated nanosensors. An imaging subsystem may detect the positions of the nanosensors. A controller may control the intensity and direction of the magnetic field in a feedback loop, in response to the detected positions of the nanosensors, so that the attractive force toward one or more injured spinal cells felt by each nanosensor because of its chemical affinity is iteratively supplemented by the magnetic levitation force applied to that nanosensor, until substantially all of the nanosensors are agglutinated around the spinal injury region.

BRIEF DESCRIPTION OF THE DRAWINGS

The figures depict one or more implementations in accordance with the present disclosure, by way of example only and not by way of limitations. The drawings disclose illustrative embodiments. They do not set forth all embodiments. Other embodiments may be used in addition or instead.

DETAILED DESCRIPTION

In the present disclosure, systems and methods are disclosed for detecting, visualizing, and imaging a spinal injury region by magnetically levitating a swarm of nanorobots each of which include a nanosensor. In one embodiment, the nanorobots may be fabricated by coating chemically sensitive nanosensors, including without limitation NO and $Ca^{2+}$ nanosensors, with a magnetic material. The nanorobots may be magnetically levitated by an external magnetic field and guided by a controller. An imaging subsystem, including without limitation a soft x-ray microscope, may be used to visualize the positions of the nanorobots. A feedback control may be implemented in response to the detected image of the nanosensors, and the magnetic levitation resulting from the external magnetic field may be controlled so as to recursively cluster the nano-robots around the spinal injury region.

Figure 1:
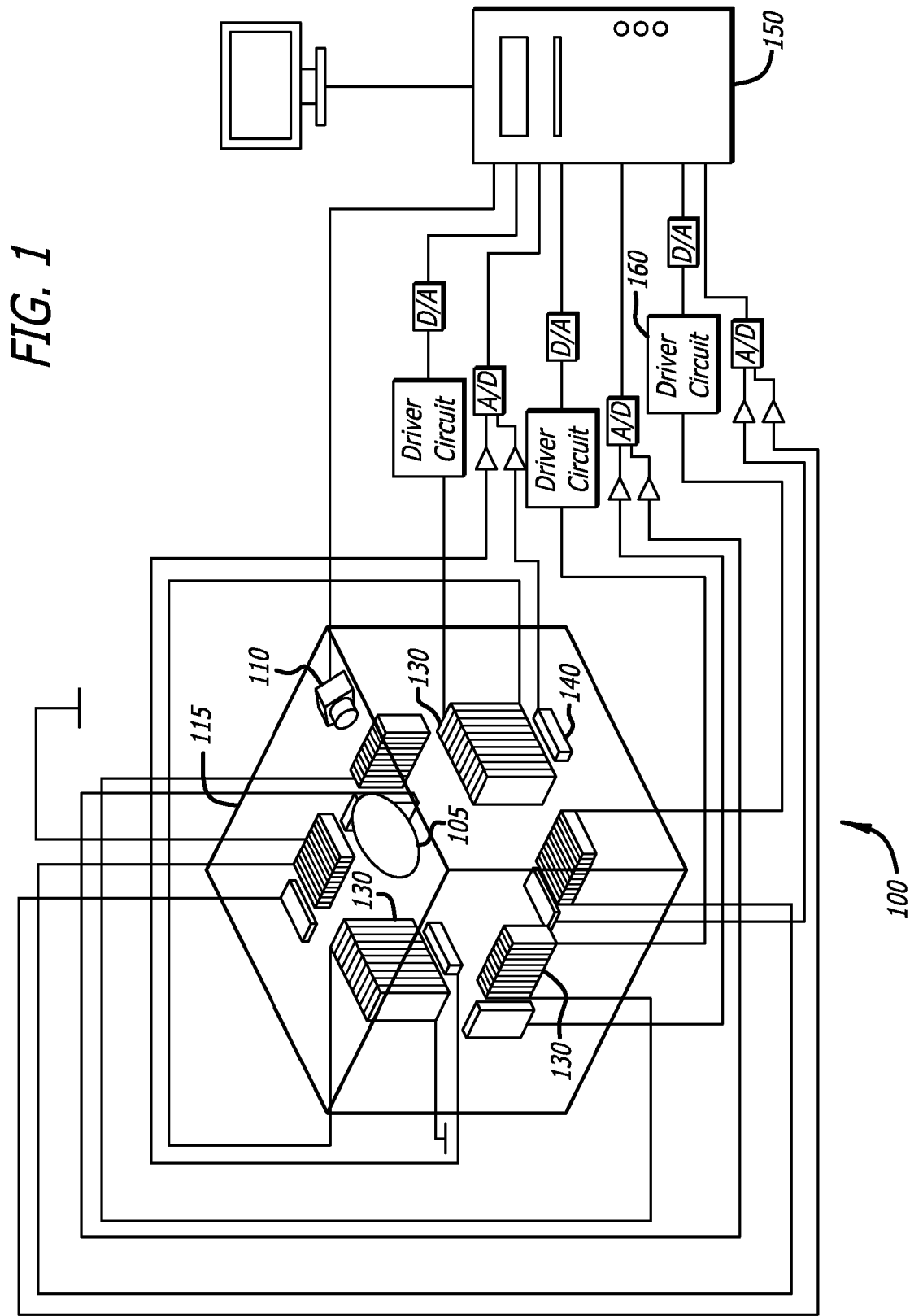
FIG. 1 illustrates a system for detecting spinal injury cells, in accordance with one embodiment of the present disclosure.

FIG. 1 illustrates a system 100 for detecting spinal injury cells, in accordance with one embodiment of the present disclosure. The system 100 utilizes a swarm 105 of magnetically levitated nanorobots to detect injured spinal nerve cells which, in the illustrated embodiment, release NO or $Ca^{2+}$. Each one of nanorobots in the swarm 105 includes at least one nanosensor. Each nanosensor has a chemical affinity that allows the nanosensor to detect one or more chemical signals released by the spinal injury cells.

In overview, the system 100 includes: a swarm 105 of the nanorobots that are coated with a magnetic material, and that are positionable in a region 115 within the cerebro spinal fluid of a patient; a magnetic field generating subsystem (further described below) that controllably generates a magnetic field that magnetically levitates the nanorobots by interacting with the magnetic material with which the nanorobots are coated; an imaging subsystem 110 that detects and monitors the 3D spatial positions of the nanorobots, and visualizes and images the nanorobots; one or more Hall effect sensors 140 that detects the 3D spatial distribution of the current magnetic field; and a controller 150. The controller 150 receives the nanosensor positions detected by the imaging subsystem 110 and the magnetic field distribution detected by the Hall effect sensors, and controls in a feedback loop the intensity and direction of the magnetic field generated by the magnetic field generating subsystem, in such a way as to progressively and iteratively supplement the attractive force that each nanosensor feels toward the one or more injured spinal cells as a result of its chemical signature by a magnetic levitation force on that nanosensor, until substantially all of the nanosensors are agglutinated around the spinal injury cells, i.e. are clustered around the specific spinal injury location, within the region 115.

In the present disclosure, the term "nanorobot" refers to an object which has an overall size on the order of a few micrometers or less in all three spatial directions, which is an assembly of nanoscopic components with individual dimensions of about 1 nm to about 100 nanometers, and which includes a nanosensor. In the present disclosure, the term "nanosensor" refers to a biological, immunological, or chemical sensor that has nanoscopic dimensions and that senses and conveys information relating to chemical signatures of injured spinal cells.

In one embodiment, the nanosensors used in the system 100 may be high sensitivity nanosensors that are configured to directly detect central nervous system chemical signals, including without limitation Nitric Oxide (NO) and/or Calcium ions ($Ca^{2+}$), which are neurochemical signatures of interest for spinal injury cell detection.

NO is a gaseous, diffusible neuronal messenger which is intrinsically involved in the mechanisms of numerous brain and/or spinal cord injury phenomena. While the role of NO remains yet to be fully deciphered, the systems and methods described in the present disclosure may direct brain researchers with directions towards a more complete understanding of events such as Spreading Depression (SD) and Ischemic injury.

Calcium ions ($Ca^{2+}$) are important for activating biological processes such as muscle contraction, protein secretion, cell death, and development. Calcium ions play an important role in the functioning of excitable cells, from the triggering of impulses in nerve cells to the regulation of biochemical pathways and basic cellular functions of all cell types in the nervous system. Calcium signaling is the main coupling mechanism linking external stimuli, via the membrane, with intracellular processes. Calcium signaling in the nervous system provides an up-to-date account of the most fundamental aspects of calcium signal generation in the nervous system, including pathways for $Ca^{2+}$ influx, buffering in the cytosol, involvement of intracellular calcium stores and $Ca^{2+}$ extrusion.

Nanosensors that include nanowire (NW) or nanotube (NT) building blocks modified with receptors or ligands for specific detection are known and have been extensively researched. In some embodiments, the nanosensors used in the system 100 may be NO nanosensors and/or calcium ion nanosensors configured to detect NO and/or $Ca^{2+}$. Such NO and $Ca^{2+}$ nanosensors have been discovered and fabricated using a number of different methods, any one of which may be used to make and use the swarm 105 of nanorobots. In other embodiments, the nanosensors used in the system 100 may be chemical nanosensors of a different kind, namely nanosensors may be used that are configured to detect chemical signals that are different from NO and/or $Ca^{2+}$.

The nanorobots in the illustrated embodiment may be fabricated by coating the NO and $Ca^{2+}$ nanosensors with a magnetic material, which may include but is not limited to $Fe_2O_3$ or neodymium. Any other magnetic material that can interact with the external magnetic field generated by the magnetic field generating subsystem may be used to coat the nanorobots.

As described above, a feedback control method may be used by the controller 150, in conjunction with a magnetic field generating subsystem to magnetically levitate the nanorobots in 3D. In the embodiment illustrated in FIG. 1, the magnetic field generating subsystem includes a plurality of solenoids 130, and associated drivers or driver circuits 160 that drive the solenoids 130 by sending and adjusting currents therethrough. In the particular embodiment described in FIG. 1, three pairs of solenoids 130 are shown as being placed along the x, y, z axes in Euler space, although different embodiments of the present disclosure may implement different configurations of the solenoids and associated driver circuits. Electromagnets may be modified by using the driver circuits 160 to adjust the current through the coils of these solenoids. Other embodiments of the present disclosure may use different geometric configurations for the solenoids and driver circuits, or may use components other than solenoids and driver circuits to controllably generate a magnetic field.

Although a theorem due to Samuel Earnshaw states that it is not possible to achieve static levitation using any combination of fixed magnets and electric charges, there are a number of ways to get around the assumptions of that theorem to dynamically achieve magnetic levitation, including but not limited to: making use of quantum effects due to electromagnetic intermolecular forces; implementing feedback control in which the strength of the electromagnets is varied to weaken the electromagnet whenever the object (being levitated) approaches the magnet, and strengthening the electromagnet when the object moves away; making use of diamagnetism, which occurs when electrons adjust their trajectories to compensate for the influence of the external magnetic field, so as to result in an induced magnetic field which has an opposite direction; making use of oscillating electromagnetic fields, which may be generated by inducing an alternating current in a conductor and thus generate a levitating force; and inducing rotation by stabilizing the direction of the magnetic moment in space.

Any one, or more, of the above-described methods may be used to achieve magnetic levitation of the swarm 105 of nanorobots, in different embodiments of the present disclosure. In embodiments in which a mechanism other than oscillating electromagnetic fields (such as quantum effects or diamagnetism) is used to levitate nanorobots, magnetic levitation devices other than a solenoid system should of course be used, since solenoids can only generate the oscillating electromagnetic fields. An illustrative hardware configuration for an exemplary magnetic levitation system is disclosed in the '051 provisional application, which is incorporated herein by reference. In other embodiments of the present disclosure, magnetic levitation systems other than the system disclosed in the '051 provisional application, including different magnetic levitation systems that are known.

The overall design of the system 100 includes a mechanism to convert the output of the nanosensors in the swarm 105 of nanorobots to a type of signal that can be identified by the observer, such as an imaging subsystem that can observe and detect the 3D positions of the nanorobots as well as the chemical detection signals emitted by the nanosensors in the nanorobots, and generate image data that can be image processed to generate visual images of the nanorobots. In the illustrated embodiment, such an imaging subsystem is a soft x-ray microscope 110. In other embodiments of the present disclosure, imaging subsystems other than a soft x-ray microscope may be used.

The imaging subsystem 110 may be a soft x-ray microscope configured to detect the output signals generated by the nanosensors, and to detect a physical center of the swarm of nanosensors. The soft x-ray microscope may, in one embodiment, have a spatial resolution of about 43 nm, although other embodiments of the present disclosure may use soft x-ray microscopes having different resolutions.

The Hall effect magnetic sensors 140 may be configured to detect and observe the 3D spatial distribution of the magnetic field.

The controller 150 controls the magnetic field generating subsystem (consisting of solenoids 130 and associated driver circuits 160, in the embodiment illustrated in FIG. 1), in response to input received from the imaging subsystem 110 and the Hall effect magnetic sensors 140, so as to recursively cluster substantially all of the nanosensors in the swarm 105 around the specific location of the spinal injury, namely around the spinal injury nerve cells. The function and operation of the controller 150 is further described in conjunction with FIGS. 2 and 3A-3C.

Figure 2:
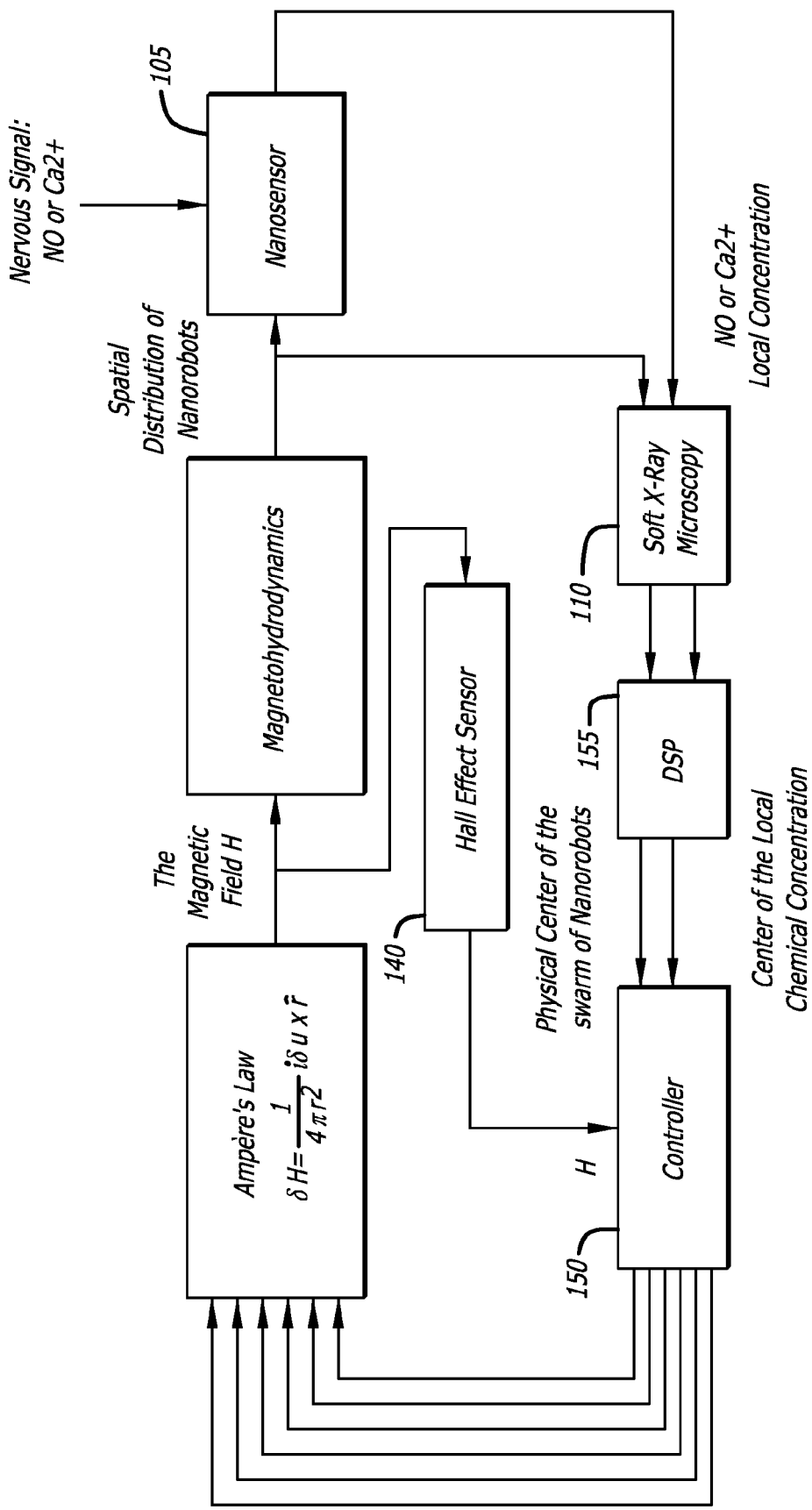
FIG. 2 is a functional block diagram illustrating the operation of the system shown in FIG. 1, in one embodiment of the present disclosure.

FIG. 2 is a functional block diagram illustrating the operation of the system shown in FIG. 1, in one embodiment of the present disclosure. As shown in FIG. 2, the controller 150 may be responsive to output signals detected by the soft x-ray microscope 110, and to the spatial distribution of the magnetic field as sensed by the Hall effect sensors 140, to compute a chemical diffusion center having a highest concentration of the chemical signals released by the injured nerve cells, and a physical center of the swarm of nanorobots, then recursively guide the physical center toward the chemical diffusion center.

As seen in FIG. 2, the Hall effect sensors 140 may be configured to use well known Ampere's Law, as well as magnetohydrohynamics equations relating to the effect of the medium (i.e. the cerebro spinal fluid present in the region 115 shown in FIG. 1) on the magnetic particles and on the magnetic field generated by the solenoids, in order to detect and observe the spatial distribution of the magnetic field generated by the solenoids 130.

In the illustrated embodiment, a DSP (digital signal processor) module 155 may be used to compute the physical center and the chemical center, and the computed output from the DSP is received by the controller 150. In one embodiment, the coordinate of the local NO or $Ca^{2+}$ density center may be obtained in the DSP module by anglicizing the distribution of the nanorobots and the output signal from their nanosensors. This coordinate may then be inputted into the controller 150 as reference for the controller 150.

The controller 150 may be responsive to the physical center and the chemical center detected by the imaging subsystem, to control the intensity and direction of the magnetic field so as to progressively guide the physical center toward the chemical center. To move the physical center of the swarm of nanorobots to the local chemical density center, the controller 150 may calculate the desired magnetic field, and compare it with the current magnetic field as observed by the Hall effect sensors. Based on this comparison, the controller 150 may progressively and recursively adjust the value of the magnetic field. For example, the controller 150 may iteratively adjust the value of the magnetic field by sending a command signal to the driver circuits 160 to adjust the value of the current sent to the solenoids 130, and/or by adjusting the position of the solenoids. The controller 150 may transfer the control decision to electrical current format, and/or the related position of solenoids if necessary, and may be synchronized by the external crystal.

Figure 3A:
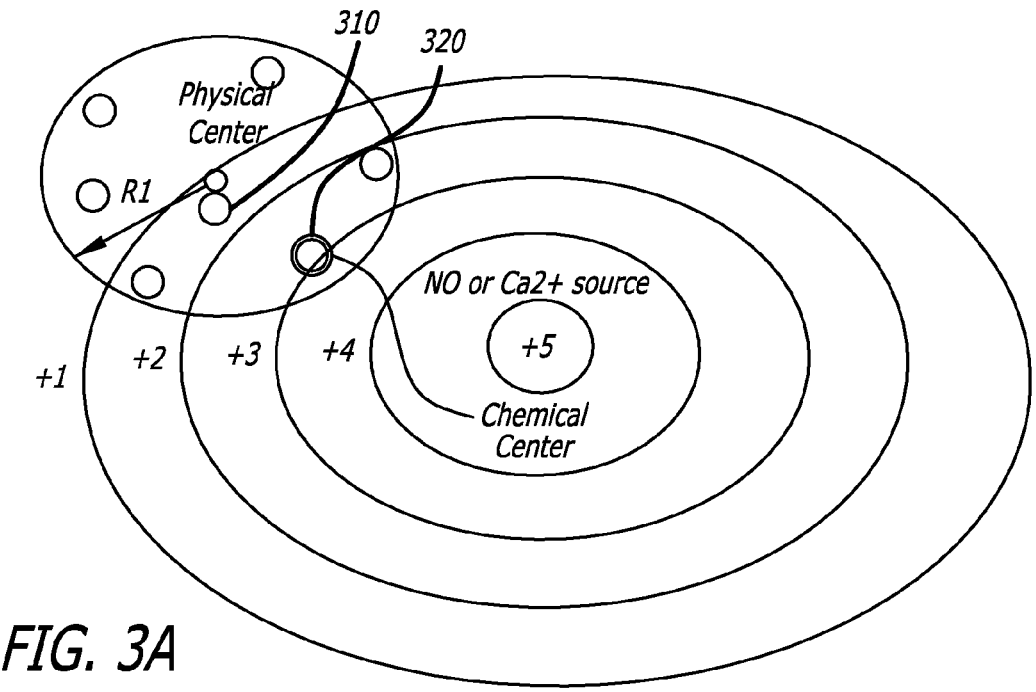
FIGS. 3A, 3B, and 3C illustrate a progressive agglutination of the swarm of nanosensors as the controller moves the physical center of the nanosensors toward the chemical diffusion center of the injured spinal nerve cells.
Figure 3B:
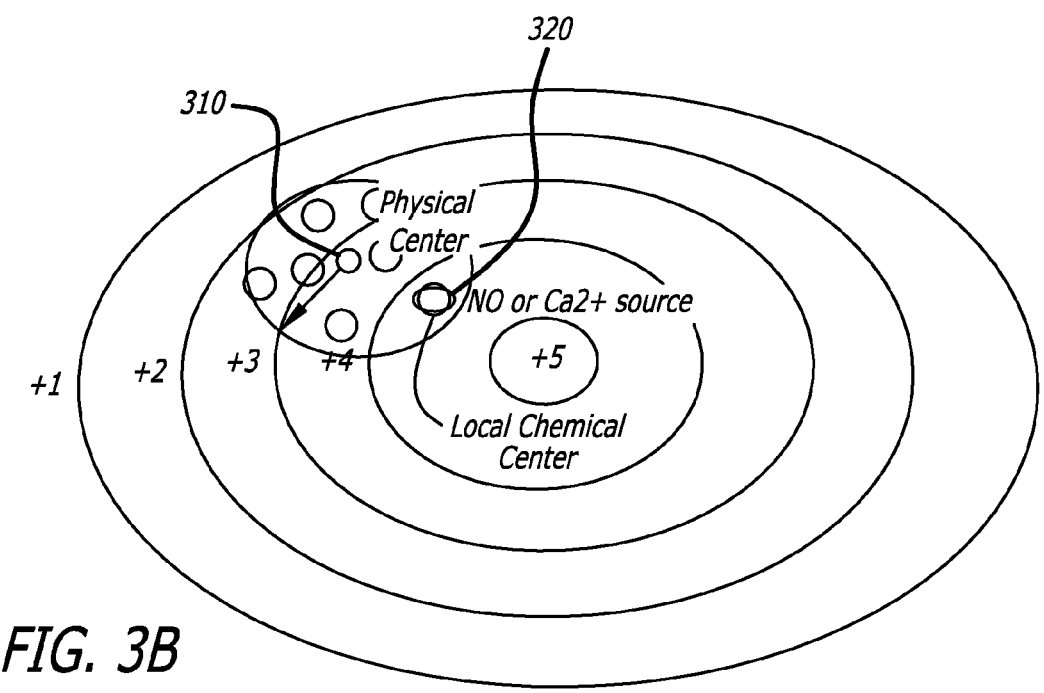
Figure 3C:
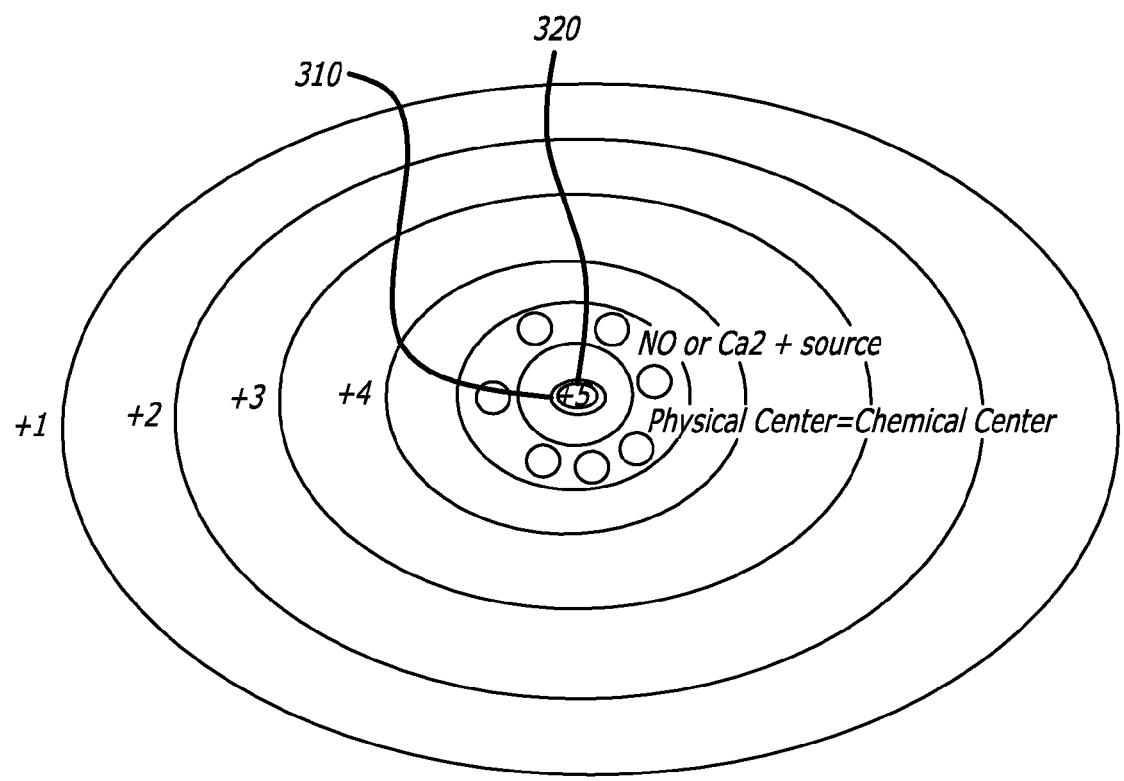

FIGS. 3A, 3B, and 3C illustrate a progressive agglutination of the swarm of nanosensors as the controller moves the physical center of the nanosensors toward the chemical diffusion center of the injured spinal nerve cells. The overall scenario that is illustrated in FIGS. 3A-3C is as follows: the swarm 105 of nanorobots is released around the area where injured spinal nervous branches may exist. The injured nervous cells release NO or $Ca^{2+}$, as explained above. The mission of the suspended nanorobots is to try to find the diffusion center of these chemical signals released by the injured nervous cells, which at the same time are likely to be the position of the injured cells.

To achieve this mission, the swarm 105 of nanorobots needs to have a proper spatial distribution to cover the potential injury area when they are injected in the beginning, as shown in FIG. 3A. Then, each nanosensor in each nanorobot begins to operate to detect the local chemical concentration. The imaging subsystem (soft x-ray microscope) 110 detects and observes a physical center 310 of the swarm 105 of nanorobots, as well as a local density center or chemical center 320, namely a local density center at which the chemical concentration of the released chemical signals (NO or $Ca^{2+}$) is the highest.

With an efficient controller 150, the external magnetic field may be controllable so as to move the physical center 310 to the chemical center 320. At the same time, the distribution area of the swarm may be decreased, and the x-ray microscope 110 may zoom in, as shown in FIG. 3B. This process may be similar to a process through which a photographer zooms a camera to find out a specific tiny object in a landscape. During this process, the nanorobots may function as guides whose goal is to detect and find objectives. The nanorobots may have to repel one another and may normally arrange themselves in a volume in the chemical diffusion areas. This self-organizing process may impart sub-stability of the nanorobots relative to each other, which would attract one another by van der Walls forces and magnetic forces under normal conditions. At time goes on, this spatial volume may be decreased, as the physical center 310 moves closer and closer to the chemical center 320.

The following steps may be iteratively repeated, in a feedback loop implemented by the controller 150: 1) compute a desired value of the magnetic field, based on the current positions of the nanorobots and the current position of the physical center 310; 2) compare the computed value with the actual magnetic field detected by the Hall effect sensors; and 3) based on the comparison, iteratively adjust the value of the magnetic field. In this way, the swarm 105 of nanorobots may be progressively and recursively guided toward the NO or $Ca^{2+}$ signal source, until substantially all of the nanorobots finally gather or cluster around the signal source, as shown in FIG. 3C.

In the aftermath of the above-described process, further observation may be applied, for example to monitor the healing process and assess the amount of regeneration of the injured nerve cells, if any, or even to repair the injured nervous cell using these nanorobots.

Figure 4:
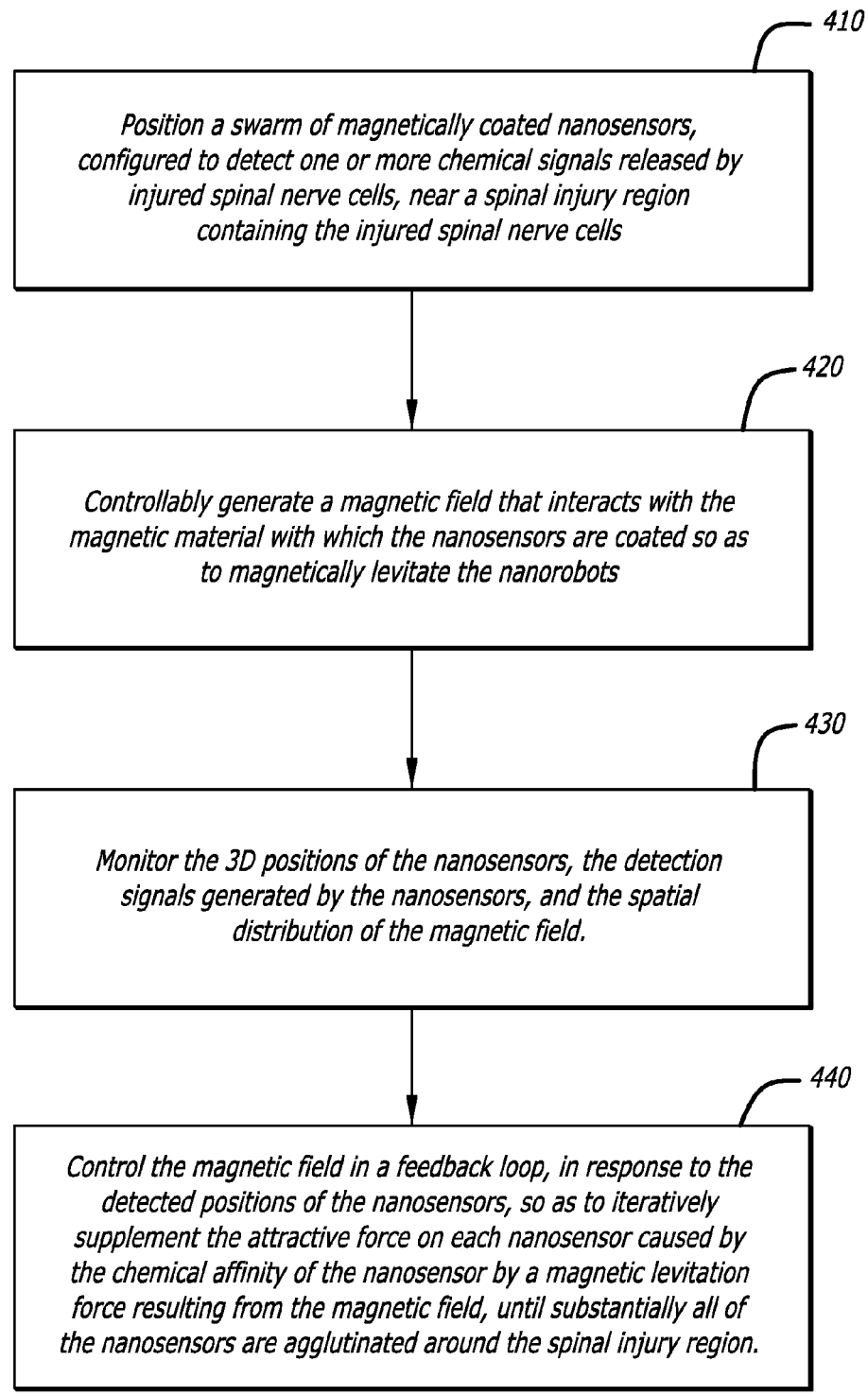
FIG. 4 is a flowchart that illustrates exemplary acts in a method of detecting spinal injury cells, in one embodiment of the present disclosure.

FIG. 4 is a flowchart that illustrates exemplary acts in a method 400 of detecting spinal injury cells, in one embodiment of the present disclosure. In the illustrated embodiment, the method 400 may include an act 410 of positioning a swarm of magnetically coated nanosensors, configured to detect one or more chemical signals released by injured spinal nerve cells, near a spinal injury region containing the injured spinal nerve cells. The method 400 may further include an act 420 of controllably generating a magnetic field that interacts with the magnetic material with which the nanosensors are coated so as to magnetically levitate the nanorobots.

The method 400 may further include an act 430 of monitoring the 3D positions of the nanosensors, the detection signals generated by the nanosensors, and the spatial distribution of the magnetic field. The method 400 may further include an act 440 of controlling the magnetic field in a feedback loop, in response to the detected positions of the nanosensors, so as to iteratively supplement the attractive force on each nanosensor caused by the chemical affinity of the nanosensor by a magnetic levitation force resulting from the magnetic field, until substantially all of the nanosensors are agglutinated around the spinal injury region.

The signal processing and control schemes described above may be implemented in part by hardware and in part by software simulation. The controller 150 as well as the imaging subsystem 110 may include one or more computers or processing systems may be used to implement the methods, systems, and algorithms described in the present disclosure.

The methods and systems in the present disclosure are not described with reference to any particular programming language. It will be appreciated that a variety of platforms and programming languages may be used to implement the teachings of the present disclosure. The processing system may be selectively configured and/or activated by a computer program stored in the computer. Such a computer program may be stored in any computer readable storage medium, including but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The methods, algorithms, and systems presented herein are not inherently related to any particular computer, platform, processor or other apparatus. Various general purpose systems may be used with different computer programs in accordance with the teachings herein. Any of the methods, systems, and algorithms described in the present disclosure may be implemented in hard-wired circuitry, by programming a general purpose processor, a graphics processor, or by any combination of hardware and software.

In sum, methods and systems have been described for using a swarm of magnetically levitated nanorobots with high sensitivity nanosensors in order to detect chemical sources, in particular the chemical signals released by injured nervous cells. The magnetically levitated nanorobots described in the present disclosure in the context of applications to the nervous system, may be coated with magnetic material and moved by an external magnetic field. The nanorobots may incorporate nanosensors that can detect chemical signals such as NO and $Ca^{2+}$ released from injured nervous cells. The sensor signals from the nanosensors may be converted to a format that can be visualized by imaging systems, including but not limited to soft x-ray microscopes. The highly charged nanorobots in the swarm may repel each other to form a colloid stabilization mechanism, and the area covered by this colloid may be decreased as the swarm moves closer to the target, namely the chemical signal center. The systems and methods described in the present disclosure may open avenues for making neural prosthetic devices and neuro-electronic interfaces.

Various changes and modifications may be made to the above described embodiments. The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

The phrase "means for" when used in a claim embraces the corresponding structures and materials that have been described and their equivalents. Similarly, the phrase "step for" when used in a claim embraces the corresponding acts that have been described and their equivalents. The absence of these phrases means that the claim is not limited to any of the corresponding structures, materials, or acts or to their equivalents.

Nothing that has been stated or illustrated is intended to cause a dedication of any component, step, feature, object, benefit, advantage, or equivalent to the public, regardless of whether it is recited in the claims.

In short, the scope of protection is limited solely by the claims that now follow. That scope is intended to be as broad as is reasonably consistent with the language that is used in the claims and to encompass all structural and functional equivalents.

What is claimed is:

1. A system for detecting the location of injured spinal nerve cells in a spinal injury region, the system comprising:
   a swarm of nanosensors, each nanosensor having a chemical affinity that interacts with a chemical released by the injured spinal nerve cells and being coated with a magnetic material;
   a magnetic field generating subsystem configured to controllably generate a magnetic field that interacts with the magnetic material so as to magnetically levitate the coated nanosensors;
   an imaging subsystem configured to detect the positions of the swarm of nanosensors and to detect the chemical interaction between the chemical affinity on the nanosensors and a density of chemical released by the injured spinal nerve cells; and
   a controller configured to:
   (a) compute a physical center of the swarm of nanosensors based on the positions detected by the imaging subsystem;
   (b) compute a local chemical center of the chemical interaction between the chemical affinity on the nanosensors and the density of the chemical released by the injured spinal nerve cells as detected by the imaging subsystem; and
   (c) control the magnetic field generating subsystem in a feedback loop so as to guide the computed physical center of the swarm of nanosensors towards the computed local chemical center; and
   (d) repeat steps (a), (b),and (c) until the positions of the computed physical center and the computed local chemical center are approximately the same, thereby causing the nanosensors to agglutinate around the spinal injury region, thereby revealing the location of the injured nerve cells.

2. The system of claim 1, wherein the chemical that is released by the injured nerve cells and that interacts with the chemical affinity on the nanosensors is at least one of Nitric Oxide (NO) and Calcium ions (Ca2+).

3. The system of claim 1, wherein the magnetic field generating subsystem comprises one or more solenoids and a driver that drives the coils of the solenoid by controllably applying electric currents therethrough.

4. The system of claim 3, wherein the magnetic field generating subsystem comprises three pairs of solenoids disposed along an x, y, and z axes.

5. The system of claim 4, further comprising one or more Hall effect sensors configured to detect a spatial distribution of the generated magnetic field.

6. The system of claim 1, wherein the imaging subsystem comprises a soft x-ray microscope.

7. The system of claim 4, wherein the controller is further configured to guide the physical center to the local chemical center by computing a desired value of the magnetic field, comparing the computed value with the magnetic field detected by the Hall effect sensors, and, based on the comparison, iteratively adjusting the value of the magnetic field.

8. The system of claim 4, wherein the controller is further configured to iteratively adjust the value of the magnetic field by one of: sending a command signal to the driver to adjust the value of current sent to the solenoids; and adjusting the position of the solenoids.

9. The system of claim 1, wherein the magnetic material comprises one of: Iron Oxide ($Fe_2O_3$) or neodymium.

10. A method of detecting the location of injured spinal nerve cells in a spinal injury region, the method comprising:
   (a) positioning near the spinal injury region a swarm of nanosensors that are coated with a magnetic material and that have a chemical affinity that interacts with a chemical released by the injured spinal nerve cells;
   (b) detecting, with an imaging subsystem, the positions of the swarm of nanosensors;
   (c) computing, with a controller, a physical center of the swarm of nanosensors based on their detection;
   (d) detecting, with the controller, the chemical interaction between the chemical affinity on the nanosensors and the chemical released by the injured spinal nerve cells;
   (e) computing, with the controller, a local chemical center of the chemical interaction between the chemical affinity on the nanosensors and the chemical released by the injured spinal nerve cells based on their detection; and
   (f) controlling a magnetic field generating subsystem in a feedback loop so as to guide the computed physical center of the swarm of nanosensors towards the computed local chemical center; and
   (g) repeating steps (b)-(f) until the positions of the computed physical center and the computed local chemical center are approximately the same, thereby causing the nanosensors to agglutinate around the spinal injury region, thereby revealing the location of the injured nerve cells.

* * * * *